(12) United States Patent
Fromm et al.

(10) Patent No.: US 10,583,223 B2
(45) Date of Patent: Mar. 10, 2020

(54) ANTIMICROBIAL SILVER COMPLEX COATED SURFACE

(71) Applicant: MEDACTA INTERNATIONAL SA, Castel San Pietro (CH)

(72) Inventors: Katharina M. Fromm, Fribourg (CH); Priscilla S. Brunetto, Lausanne (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 0 days.

(21) Appl. No.: 15/513,603

(22) PCT Filed: Sep. 21, 2015

(86) PCT No.: PCT/IB2015/057259
§ 371 (c)(1),
(2) Date: Mar. 23, 2017

(87) PCT Pub. No.: WO2016/046725
PCT Pub. Date: Mar. 31, 2016

(65) Prior Publication Data
US 2017/0239394 A1    Aug. 24, 2017

(30) Foreign Application Priority Data

Sep. 23, 2014  (IT) .............. MI2014A1644

(51) Int. Cl.
| | | |
|---|---|---|
| *A61L 27/54* | (2006.01) | |
| *A61L 27/04* | (2006.01) | |
| *A61L 27/30* | (2006.01) | |
| *A61L 27/28* | (2006.01) | |

(52) U.S. Cl.
CPC .......... *A61L 27/54* (2013.01); *A61L 27/045* (2013.01); *A61L 27/28* (2013.01); *A61L 27/306* (2013.01); *A61L 2300/104* (2013.01); *A61L 2300/404* (2013.01); *A61L 2300/606* (2013.01); *A61L 2420/02* (2013.01); *A61L 2430/02* (2013.01); *A61L 2430/12* (2013.01)

(58) Field of Classification Search
CPC .......... A61L 2300/104; A61L 2430/12; A61L 27/045; A61L 27/28
See application file for complete search history.

(56) References Cited

U.S. PATENT DOCUMENTS

| | | | | |
|---|---|---|---|---|
| 4,116,724 A * | 9/1978 | Hirschfeld | .............. | C22C 19/07 148/425 |
| 2005/0048193 A1 * | 3/2005 | Li | ............. | A61F 2/30767 427/2.24 |
| 2006/0161256 A1 | 7/2006 | Ziegler et al. | | |
| 2008/0195214 A1 * | 8/2008 | Chiba | ............. | A61L 27/045 623/18.11 |
| 2009/0035341 A1 | 2/2009 | Wagener et al. | | |
| 2011/0189493 A1 | 8/2011 | Ott et al. | | |

OTHER PUBLICATIONS van Hove, R.P et al. "Differences in proliferation, differentiation, and cytokine production by bone cells seeded on titanium-nitride and cobalt-chromium-molybdenum" Journal of Biomaterials Applications 2012, 28(2) 278-287 (Year: 2012).*
Slenters, T.V. "Novel silver containing antimicrobial coatings for implant materials: new applications of Ag(I) coordination networks" Dissertation, 2009, p. 1-212. Available: http://edoc.unibas.ch/1011/1/TheseTVS_toPDF.pdf (Year: 2009).*
Matinlinna, J.P et al. "Surface analysis of Co—Cr—Mo alloy and Ti substrates silanized with trialkoxysilanes and silane mixtures" Surf. Interface Anal. 2004; 36: 246-253 (Year: 2004).*
Ballarre, J et al., "In vivo and in vitro evaluation of vitreous coatings on cobalt base alloys for prosthetic devices", Journal of Non-Crystalline Solids, North-Holland Physics Publishing. Amsterdam, NL, vol. 304, No. 1-3, Jun. 1, 2002, pp. 278-285.
Eurocoating, Plasma spray coatings, Ti Growth, available at http://www.eurocoating.it/plasma_spray_coatings/growth/default.aspx (accessed on Mar. 23, 2017).
Greulich et al., "Studies on the biocompatibility and the interaction of silver nanoparticles with human mesenchymal stem cells (hMSCs)", Lagenbecks Arch. Surg., 2009, 394, pp. 495-502.
Preetsch et al., "Silver-doped calcium phosphate nanoparticles:Synthesis, characterization, and toxic effects toward mammalian and prokaryotic cells", Colloids and Surfaces B: Biointerfaces, 2013, 102, pp. 724-729.
Tünde Vig Slenters et al., "Silver coordination compounds as light-stable, nano-structured and anti-bacterial coatings for dental implant and restorative materials", Journal of Materials Chemistry, vol. 18, No. 44, Jan. 1, 2008, p. 5359-5362.
Tünde Vig Slenters et al., "Of Chains and Rings: Synthetic Strategies and Theoretical Investigations for Tuning the Structure of Silver Coordination Compounds and Their Applications", Materials, vol. 3, No. 5, May 25, 2010, pp. 3407-3429.
International Search Report and Written Opinion dated Jan. 1, 2016, from International Application No. PCT/IB2015/057259, 10 pages.
"Metal Foams: A Design Guide," Ed. MF Ashby, Butterword Heinemann, 2000.
Zheng et al. "Sputtered Titanium Nitride Films on Titanium Foam Substrates as Electrodes for High-Power Electrochemical Capacitors," ChemElectroChem, 2018, 5, 2199-2207.

* cited by examiner

*Primary Examiner* — Andrew S Rosenthal
(74) *Attorney, Agent, or Firm* — Meunier Carlin & Curfman LLC (57) ABSTRACT

The present invention relates to orthopedic implants, in particular to hip and knee prostheses, substantially involving metallic substrates with an antibacterial surface treatment consisting of silver immobilized in an organic linker and ligand via a multistep solution dipping and drying process. This treatment while being biocompatible is designed to inhibit bacterial growth and therefore combat periprosthetic infection which is one of the main causes of revision in hip and knee arthroplasty.

13 Claims, 6 Drawing Sheets

ANTIMICROBIAL SILVER COMPLEX COATED SURFACE

FIELD OF THE INVENTION

The present invention refers to an antimicrobial surface made of a chromium-cobalt molybdenum (CrCoMo) alloy, coated with a silver (Ag+) complex derivative. The thus obtained surface can be for instance useful for the preparation of orthopedic implants, as well as for the preparation of dental implants.

STATE OF THE ART

Periprosthetic infection remains a dangerous consequence of implant insertion; it is caused by surgical contamination as well as haematogenous sources: bacteria colonize the implant surfaces and form a biofilm that is resistant to immune surveillance.

The average occurrence of such infection is in the range of 1% of all hip and knee arthroplasties. However there is a 10% likelihood of a further revision surgery within 2 years of a revision following an implant related infection. This higher incidence can be explained by the fact that within the revision (re-operation) of a joint, an implant has to be removed and a new one has to be implanted, increasing the infection risk. The treatment of an infection can result in long hospitalization, revision procedures and sometimes death. The strategies to prevent periprosthetic infection involve the formation of antibacterial surfaces on the orthopedic implants. The surface has an antibacterial effect if:
a) prevents bacterial adhesion: the surface is "lubricious" (for example hydrogel coatings or cross linked silicon containing coating layer such as in patent application EP2318060),
or
b) destroys the bacteria (or restrict their number) when they reach the surface and therefore avoid biofilm formation,
or
c) disrupts the biofilm after its formation.

A lot of antimicrobial coatings involve not only silver but also copper, antibiotics, peptides, chitosan or even mixture thereof.

US2009035341, for example, discloses an antimicrobial non-cytotoxic coating composition comprising a biocide layer selected from silver, copper and zinc and mixture thereof.

However, the stringent orthopedic requirements related to long term implantation and sterility assurance have restricted the list of possibilities mainly to antibiotics and silver ions. As examples, there can be cited Gentamycin and Rovamycin, that have been successfully covalent bonded to titanium implant surfaces, and silver coordination networks based on isonicotinic acid, used for the coating of some substrates such as, in particular, gold and titanium.

Vig Slenters et al (Journal of Materials Chemistry, 2008, 18, 5359-62) describe the use of some isonicotinic derivatives for the coating of titanium or gold alloy substrates, useful as orthopedic implants.

Saguè et al. (materials 2010, 3, 3407-29) describe some other INA (isonicotinic acid) linkers, employable for the preparation of antimicrobial surfaces.

It is worth noting that the diversity of material forming the coated substrates can play a crucial role in the biocompatibility and in the efficacy of action of the antimicrobial prosthesis. In general, titanium substrates are the most commonly used ones, due to the versatility and easiness of manufacturing.

US20060161256 describes a method for the preparation of a biocompatible coated titanium oxide substrate, useful in orthopedic implantations.

Even if the titanium oxide represents a valid substrate for this kind of applications, it has to be considered that the titanium coated prosthesis can show a bone integration that can be not as good as expected. During the wear, in fact, it has been observed that small particles of titanium oxide are removed from the surface, causing development of inflammation nearby the implant. The infection thus caused is just one of the series of problem potentially related to the use of antimicrobial silver coated titanium oxide prosthesis.

There is thus the need to find a material which can be used for the preparation of orthopedic or dental prosthesis, highly biocompatible, and which is able to prevent the above cited infections, thus decreasing the healing time and the medical costs.

The Applicant has now found that the aforementioned problems can be overcome by using a silver coated alloy material, characterized by the fact that said material is made with an alloy composed of: chromium, cobalt and molybdenum (herein generally indicated with Cr—Co—Mo alloy). The antimicrobial material of the invention can be conveniently applied either in orthopedic or in dental sector, allowing the realization of prosthesis endowed with high safety and antimicrobial action as set forth in the herein enclosed experimental part.

SUMMARY OF THE INVENTION

In one aspect, the present invention relies on a Chromium-Cobalt-Molybdenum alloy (here indicated as CrCoMo) material of formula (I):

[Ag+--Ligand--Ag+]--[linker]-----CrCoMo     (I)

wherein:
CrCoMo is an alloy substrate comprising Chromium, Cobalt and Molybdenum,
---- is a coordination or a covalent bond;
-Ligand- is a divalent group selected from:

wherein:

X=O, S, NH
n=1 or 2

-linker- is a divalent group selected from:

wherein:

m=1, 2, 3, or 4
X=O, S, NH
wherein the terminal aromatic rings of the linker or the ligand are heteroaromatic rings, preferably having at least one heteroatom such as nitrogen in place of a carbon atom; the terminal rings of the linker or the ligand can optionally be substituted with one or more —$NH_2$ group,
and wherein, the ligand binds the Ag+ ions by the at least one heteroatom of the terminal aromatic rings, preferably by a pyridine nitrogen atom; wherein the linker binds the Ag+ atom by the at least one heteroatom of one terminal aromatic ring, preferably by a pyridine nitrogen atom, and the CrCoMo surface by an atom selected from: O, N and S.

In and additional aspect, the invention refers to the use of said material in orthopedic or dental sector.

In another aspect the invention refers to orthopedic or dental prosthesis made with the coated material of the invention.

In a further aspect, the present invention refers to a process for the preparation of the above coated material, comprising the steps of:
1) gritblasting the surfaces of CrCoMo alloys to be coated, to achieve a controlled roughness,
2) alkaline washing and drying the gritblasted surface,
3) acidic passivation of the thus treated alloy material,
4) linker deposition with isonicotinic acid,
5) silver compound dip-coating or spraying, and drying,
6) multistep biological washing, and optionally
7) packaging and gamma rays sterilization.

DETAIL DESCRIPTION OF THE INVENTION

The term "$C_1$-$C_4$Alk" means a linear or branched divalent alkyl chain, having from 1 to 4 carbon atom, such as: —$CH_2$—, —$CH_2$—$CH_2$— and the like.

The present coated CrCoMo alloy is particularly useful for the realization of orthopedic prosthesis, being easy to prepare, endowed with a high biocompatibility, and designed to inhibit bacterial growth thus preventing periprosthetic infection.

In a preferred embodiment of the invention, in both the ligand and the linker structures of formula (I), the terminal aromatic rings are pyridines, substituted in para position with the R/R1 group.

In more details, the present CrCoMo alloy is preferably coated with a complex according to formula (I) wherein the ligand has the above indicated formula wherein X=oxygen.

Still preferred are ligands wherein n=2.

In a more preferred embodiment, the ligand moiety is a pyridine derivative of formula:

wherein the two terminal pyridine nitrogen atoms each binds a silver ion (Ag+). In a preferred embodiment, the alloy of the invention is coated with a linker of general formula:

wherein:

-continued and m=1, 2, 3, or 4.

Preferably, R is in para position, and the ring is a pyridine cycle.

Figure 6:
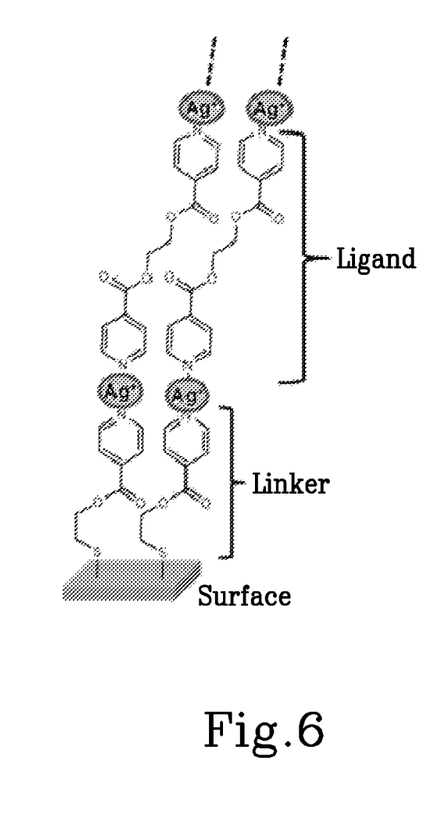
FIG. 6: schematic representation of a preferred embodiment of the invention.

Particularly preferred are linkers wherein the group $(CH_2)_m$ in the above indicated R group is a —$CH_2$—$CH_2$— moiety, as for instance indicated in the preferred embodiment showed in FIG. 6.

In this embodiment of the invention, the divalent linker binds on one side the surface by thiol sulfur atom, and on the other terminal side an Ag+ ion by the pyridine nitrogen atom; whereas the ligand binds this latter Ag+ ion by a pyridine nitrogen atom, and another Ag+ ion on the other end by a pyridine nitrogen atom as well.

The CrCoMo alloy used in the present invention is a CoCrMo ISO 5832-12, conventionally used for orthopedic implants. This alloy contains 26-30% of Cr, 5-7% of Mo, 1% of Ni, 0.75% of Fe, 1% of Mn, 1% of Si, 0.25% of N and 0.14-0.35% of C.

In an embodiment according to the invention, the CrCoMo alloy can be coated with a metallic foam, preferably a titanium foam, which can be applied on the alloy using a thermal spray technology, known in the art, for example from http://www.eurocoating.it/plasma_spray_coatings/growth/default.aspx.

The metallic coating is applied before the alloy is coated with the complex of formula (I).

The alloy material of the invention can be partially or completely coated with the antimicrobial composition comprising the complex of formula (I) as herein set forth.

"Partially coated" means that the alloy material has a percentage of coated surface up to 80%, whilst "completely coated" means that the material is coated from 80 to 100% of its surface.

Preferably, the material has a coated surface comprised from 70 to 90% of its surface.

The applicant has found that such alloy composition can be easily loaded with the above described Ag+/linker/ligand system, avoiding nevertheless the major problems related to the use of titanium oxide alloys.

The complex of formula (I) of the invention can be prepared by mixing the ligand and the appropriate silver salt, for instance as described in Journal of Materials Chemistry, 2008, 18, 5359-62, in the presence of a polar organic solvent such as a lower alcohol (i.e. having a number of carbon atoms from 1 to 4), THF, $CH_3CN$ and the like.

According to the present invention, the linker moiety binds the surface of the Cr—Co—Mo alloy preferably via covalent bonds, thus ensuring a strong and durable attachment thereto. Such polymeric network can then act as reservoir of silver (Ag+) ions and is capable of releasing bactericidal levels of Ag+ ions for an extended period of time at a safe concentration. In this way, the resulting material is endowed with: light and mechanical stability, long term antimicrobial activity, reproducibility, non-toxicity and high bio-integration.

In a further aspect, the invention refers to the use of the above described Cr—Co—Mo alloy coated material of formula(I) in orthopedic or dental field, in particular for the preparation of orthopedic or dental implants. In this regard, preferred orthopedic implants of the invention are selected from: hip, knees, shoulder, wrist and spine.

Advantageously, said implants can be prepared by only minor modifications in the current prosthesis manufacturing process, also reducing infections that have damaging effect on the patient health.

The present invention also refers to a process for the preparation of the above described antimicrobic material. In a preferred embodiment of the invention, the manufacturing process involves the following steps of:

1) gritblasting the surface of CrCoMo alloy to coat to achieve a controlled roughness.
2) Alkaline washing with a ethanolamine in an ultrasonic bath followed by drying in oven to remove the oily residues and debris;
3) Passivation with citric acid or nitric acid or sulfuric acid;
4) Linker deposition, using dip-coating or spraying, for a time ranging from a few hours to 5 days;
5) Applying the silver compound using dip-coating or spraying technique; 6) Multistep washing in an ultrasonic bath;
a) sodium and potassium metasilicate then citric acid neutralization;
or b) enzymatic wash followed by metasilicate and ethanolamine wash;
or c) wash using other solvents such as hydrofluoro ether and isopropyl alcohol vapour
and optionally
7) packaging and gamma rays (25 Krays) sterilization.

The orthopedic products made of Cobalt Chromium Molybdenum alloys and manufactured with the above described process have the following surprising characteristics at the moment of use:
a) they contain measurable amount of silver on their surfaces;
b) they release silver ions (Ag+) in body fluid for at least 24 days;
c) they inhibit the bacterial development of *Staphylococcus aureus* and *Staphylococcus epidermis* at their contact (Kirby-Bauer Test);
d) the linker/ligand coating survives the washing steps;
e) the linker/ligand coating survives the gamma sterilization cycles. Prior art indicates that ligand exhibits light stability but 25 Krays applied during gamma sterilization has a high radiation energy than light aging with a "15 watts bulb at 10 centimeters for months" (see for instance Vig Slenters et al. Journal of Materials Chemistry, 2008, 18, 5359-62).
f) the mouse cell line (L-929) is not compromised despite other publications on other silver based compounds (see for example Peetsch et al. colloid surfaces B, 2013, 102, 724-29). The silver coordination networks are made relatively insoluble in water and therefore they keep the silver ion release below the cytotoxic limit. It is however surprising that the low solubility does not compromise bacterial inhibition, even after radiation sterilization.

The invention will be now described with the following not limiting experimental part

EXPERIMENTAL PART

Example 1: Preparation of the Antimicrobial Composition Comprising a Complex of Formula (I) (General Procedure)

A solution of Linker (L) INA derivative (one or two equivalents depending on the desired ratio M:L) in solvent THF is introduced in one side of the tube, a solution of silver salts (AgX) in $H_2O$ or EtOH or $CH_3CN$ being introduced on the other side. Both solutions are frozen and the diffusion solvent THF is added to connect both. The tube stays then at room temperature in darkness and diffusion can occur.

Slow Diffusion:

One (or two) equivalent of silver salt (depending on the desired ratio M:L) and one equivalent of ligand are mixed in $CH_3OH$, THF or $CH_3CN$. The reaction occurs during ca. 24 hours at room temperature. In the case of solubility problems, the reaction solution in the Schlenk tube is heated under reflux. After filtration, the method of slow diffusion is used to obtain a single crystalline product. In the bottom of the flask the mother solution is deposited, representing ca. 30% of the total volume of the solution. On top of this, a second phase of solvent (hexane, $CH_3CN$ or THF) is carefully layered with a syringe in order not to mix the two phases. Slow diffusion occurs at room temperature.

Example 2: Preparation of a Silver Coated Co—Cr—Mo Alloy Surface According to the Invention Discs of 10 mm diameter and 2 mm thickness made out of CoCrMo ISO 5832-12 were gritblasted with alumina microspheres on one face in order to obtain a roughness factor (Ra) of 3 microns. They were subjected to the manufacturing coating process of the invention with the following process parameters:
  Alkaline wash with Deconnex (MEA) during 12 minutes,
  Passivation with nitric acid (32%) for 1 hour at room temperature,
  INA (5 mM) linker deposition during 3, 5, 24 and 120 hours,
  L1AG (2 mM) coated and dried twice for 3 hours,
  HFE/IPA solvent wash, The discs were either packaged and gamma sterilized (see results in example 3.1) or not sterilized (see results in Example 3.2).

Example 3: Antimicrobial Activity

The sterilized and the not-sterilized discs of the invention obtained in Example 2 have been subjected to some analytical and in vitro analysis as herein above described.

Figure 1:
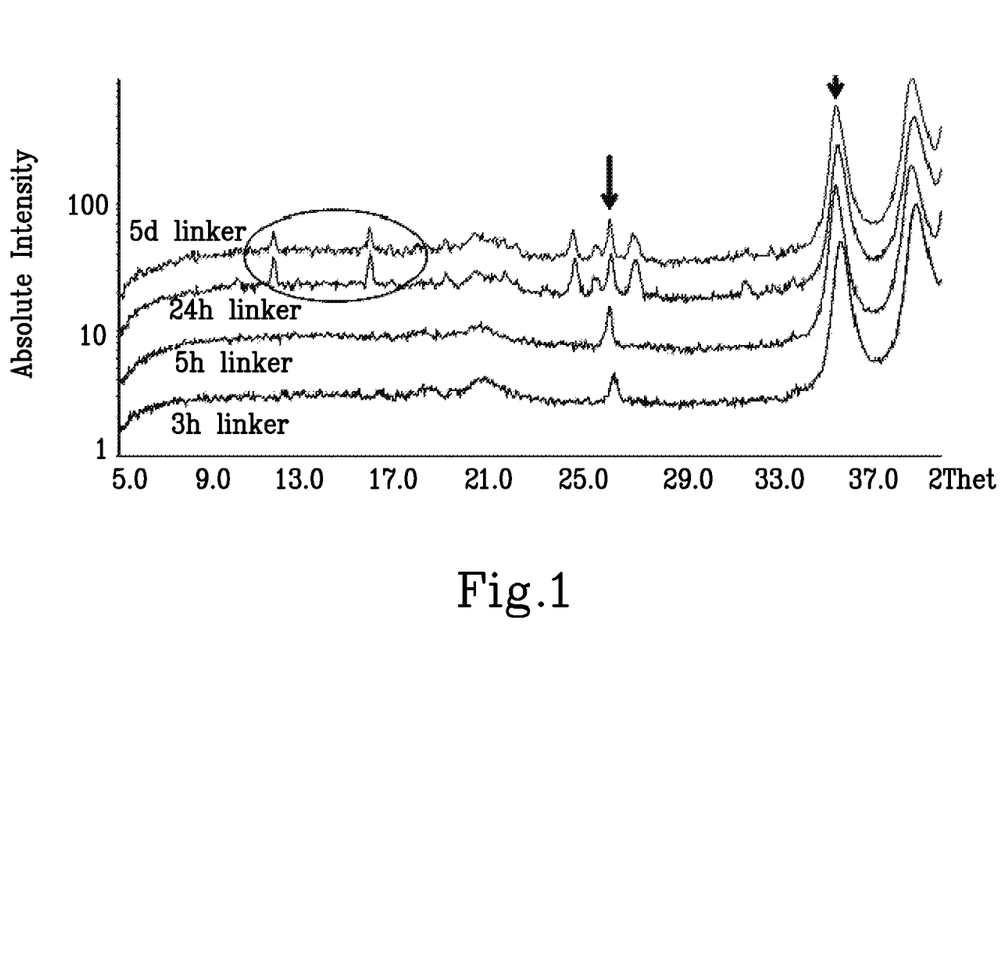
FIG. 1: XRD diffractogramm of silver-compound coated on CrCoMo alloy surface of example 3.1
Figure 2:
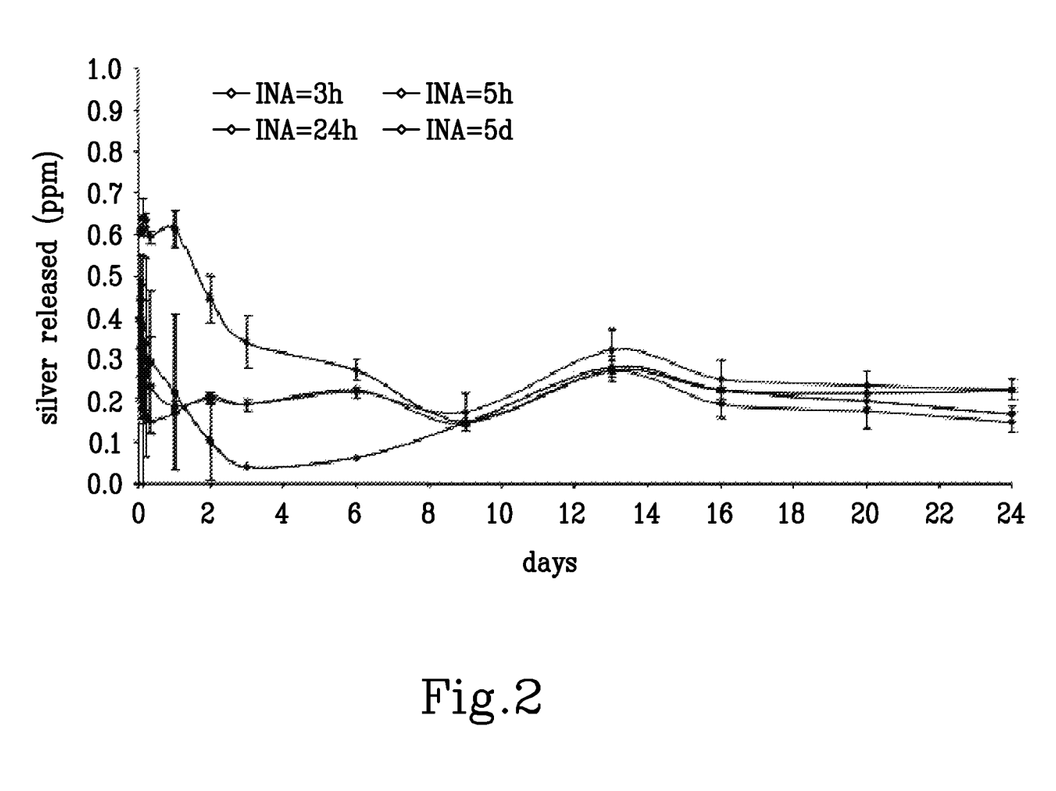
FIG. 2: Silver release profile of the coated CrCoMo alloy surface of example 3.1.
Figure 3:
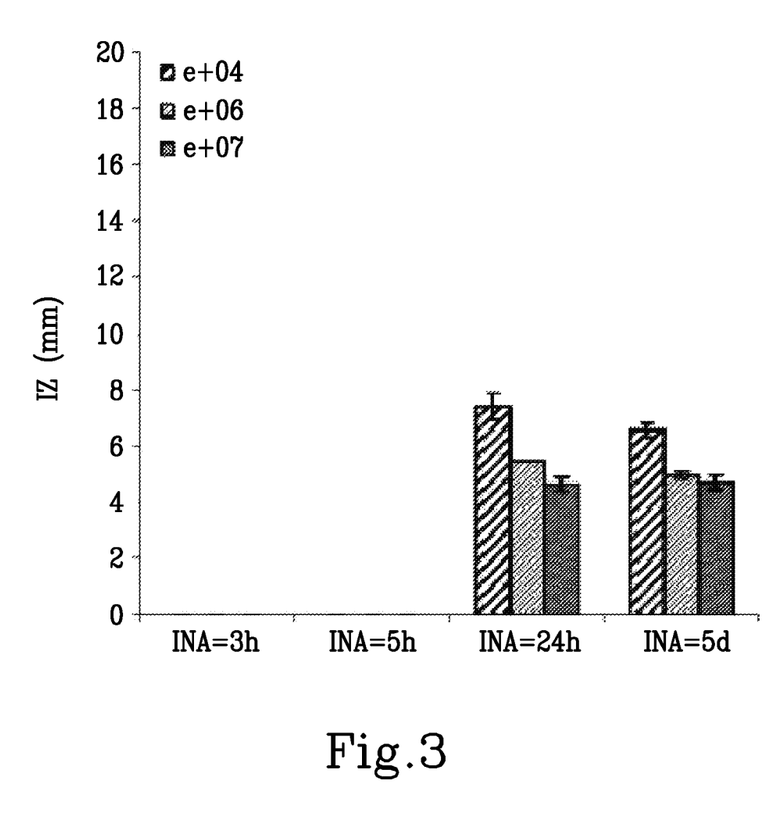
FIG. 3: In vitro Kirby-Bauer test on silver-compound coated CrCoMo surface with three different loading of *S. aureus* of Example 3.1.

3.1 Non-Sterilized Discs a) Surface X-Ray diffraction (silver-compound coated alloy surfaces were submitted to the X-Ray diffraction beam) confirmed the presence of silver on the surface for linker deposition of 24 and 120 hours (see FIG. 1).

b) ICP-OES (inductively coupled plasma optical emission spectrometry) measurements in PBS (silver-compound coated alloy surfaces were immersed in PBS solution for a determined time before being placed in another PBS solution for the following times; the removed solutions from each surface were diluted in water with nitric acid and submitted to the measurement) indicated an Ag+ ion release during at least 24 days (see FIG. 2).

c) In vitro Kirby-Bauer test (coated alloy surfaces were placed in a Petri-dish plate layered by a Muller-Hinton Agar mixture containing different bacterial loads; after a 24 h incubation time at 37° C., antimicrobial activity was verified with the appearance of a zone of inhibition that remained free from microbial growth) indicated an inhibition zone with *S. aureus* for linker deposition of 24 and 120 hours (see FIG. 3).

3.2 Sterilized Discs

Figure 4:
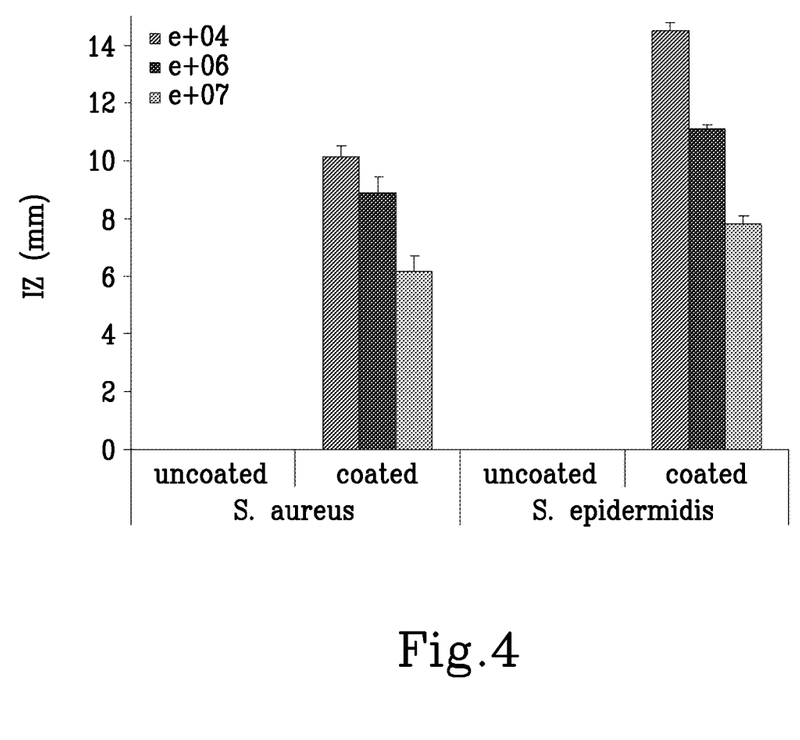
FIG. 4: In vitro Kirby-Bauer test on CrCoMo alloys surface with three different loading of *S. epidermidis* and *S. aureus* (10e+04, 10e+6, 10e+07) of example 3.2.

In vitro Kirby-Bauer bacterial inhibition tests were performed with *S. aureus* and *S. epidermis* strains CoCrMo discs after sterilization: it is surprising to evidence a large inhibition zone with both strains despite of the numerous treatments (washing and sterilization) applied to these discs (see FIG. 4).

Figure 5:
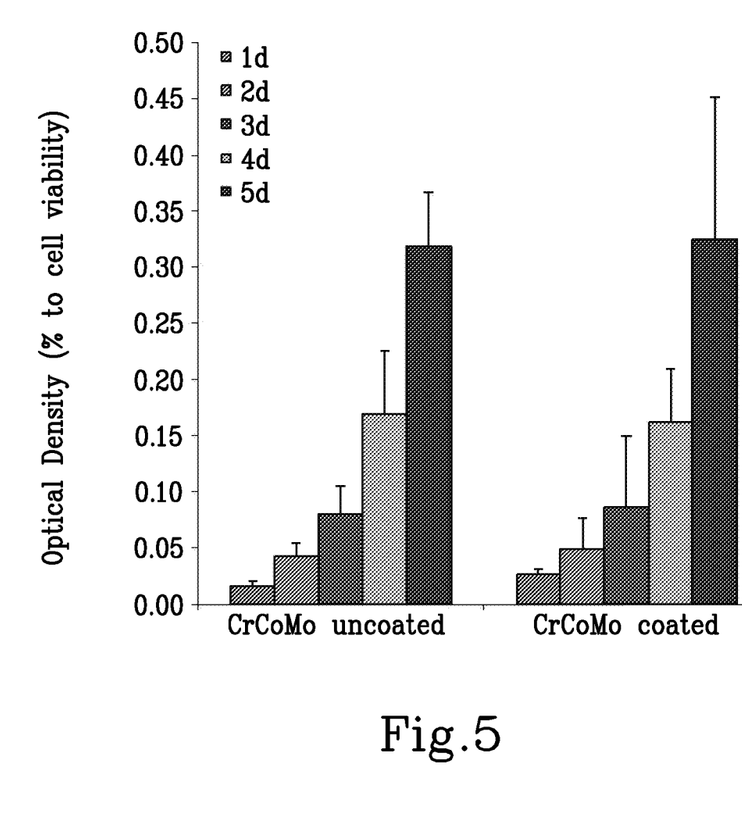
FIG. 5: In vitro cell viability based on MTT assay of both silver-compound coated CrCoMo alloy surfaces performed at 24 h, 48 h and 72 h of culture of example 3.2.

L-929 cell lines remain still alive on both surfaces after 3 and 5 days as measured by optical density (cell viability was evaluated on a colorimetric MTT based assay measuring the activity of cellular enzyme that reduce the tetrazolium dye MTT to its insoluble formazan, giving a purple color; silver-compound coated alloy surfaces were pre-incubated in the culture medium prior to cell seeding and after 24 h, 48 h, 72 h, 96 h and 120 h of culture, MTT reagent was added in each surfaces at 37° C. for 3 h leading to the formazan formation detectable in optical spectrometry) (see FIG. 5).

This result is surprising as other studies made on other silver-coated materials indicate a significant cytotoxicity (see for instance A. Peetsch et al. Colloid Surfaces B, 2013, 102:724-729, and C. Greulich et al. Langenbecks Arch Surg, 2009, 394:495-502).

The invention claimed is:

1. A coated Chromium-Cobalt-Molybdenum alloy material of formula (I):

wherein:
CrCoMo is an alloy substrate comprising Chromium, Cobalt and Molybdenum;
---- is a coordination or a covalent bond;
-Ligand- is a divalent group selected from:

wherein:

X═O, S, NH;
n=1 or 2;
-linker- is divalent group selected from:

wherein:

m=1, 2, 3, or 4;
X=O, S, NH;
wherein the terminal aromatic rings of the linker or the ligand are heteroaromatic rings having at least one nitrogen in place of a carbon atom; the terminal rings of the linker or the ligand can optionally be substituted with one or more —NH$_2$ group;
wherein the ligand binds the Ag+ ions by the at least one nitrogen atom of the terminal aromatic rings; and
wherein the linker binds the Ag+ atom by the at least one heteroatom of one terminal aromatic ring and the CrCoMo surface by an atom selected from: O, N and S.

2. The alloy material of claim 1, wherein X=oxygen.
3. The alloy material of claim 1, wherein n=2.
4. The alloy material of claim 1, wherein the ligand moiety is a pyridine derivative of formula:

in which the two terminal pyridine nitrogen atoms each binds a silver ion (Ag+).
5. The alloy material of claim 1, wherein the linker has the general formula:

wherein:

where m=1, 2, 3, or 4.
6. The alloy material of claim 5, wherein R is:

7. The alloy material of claim 1, wherein the CrCoMo substrate contains 26-30% of Cr, 5-7% of Mo, 1% of Ni, 0.75% of Fe, 1% of Mn, 1% of Si, 0.25% of N and 0.14-0.35% of C.
8. An orthopedic or dental prosthesis made with the alloy material of claim 1.
9. A process for the preparation of the alloy material of claim 1, comprising the steps of:
   1) gritblasting the surface of a CrCoMo alloy material to be coated, to achieve a controlled roughness,
   2) alkaline washing and drying the alloy material,
   3) acidic passivation of the thus treated alloy material,
   4) linker deposition on the surface,
   5) mixing the ligand and a Silver compound to form the [Ag+--Ligand--Ag+], which is then deposited by dip-coating or spraying and drying,
   6) multistep washing, and optionally
   7) packaging and gamma rays sterilization.
10. The alloy material of claim 1, wherein the ligand binds the Ag+ atom by a pyridine nitrogen atom of at least one terminal aromatic ring.
11. The alloy material of claim 1, wherein the linker bonds the Ag+ atom by a pyridine nitrogen atom of a terminal aromatic ring.
12. The alloy material of claim 1, wherein the CrCoMo alloy substrate is coated with a metallic foam.
13. The alloy material of claim 1, wherein the CrCoMo alloy substrate is coated with a titanium foam.

* * * * *